US008329461B2

(12) United States Patent
Marek et al.

(10) Patent No.: US 8,329,461 B2
(45) Date of Patent: Dec. 11, 2012

(54) HANDHELD IMPLEMENT FOR REMOVING MICROBIOLOGICAL MATTER FROM A SURFACE

(75) Inventors: Patrick J. Marek, Shrewsbury, MA (US); Joshua P. Magnone, Millis, MA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 535 days.

(21) Appl. No.: 12/539,329

(22) Filed: Aug. 11, 2009

(65) Prior Publication Data

US 2011/0035898 A1    Feb. 17, 2011

(51) Int. Cl.
*C12M 1/26* (2006.01)

(52) U.S. Cl. .............. 435/309.1; 600/571; 422/128; 422/406

(58) Field of Classification Search .......... 435/309.1; 422/127, 128, 406, 411; 15/221, 344; 184/22, 184/25, 102; 206/361; 604/1, 3; 73/864.41, 73/864.71, 864.72; 600/565, 569, 572, 573
See application file for complete search history.

(56) References Cited

U.S. PATENT DOCUMENTS

| 3,724,018 | A | | 4/1973 | Sills |
|---|---|---|---|---|
| 4,376,634 | A | * | 3/1983 | Prior et al. .................. 435/18 |
| 5,084,005 | A | | 1/1992 | Kachigian |
| 5,084,245 | A | * | 1/1992 | Berke et al. ................ 422/411 |
| 5,158,532 | A | | 10/1992 | Peng et al. |
| 5,354,956 | A | * | 10/1994 | Orban et al. ............... 181/105 |
| 5,569,279 | A | | 10/1996 | Rainin |
| 6,624,133 | B1 | | 9/2003 | McKenzie et al. |
| 7,032,269 | B2 | | 4/2006 | Mikhaylichenko et al. |
| 2005/0136553 | A1 | * | 6/2005 | Kaylor et al. .............. 436/518 |
| 2007/0244368 | A1 | * | 10/2007 | Bayloff et al. ............. 600/300 |

* cited by examiner

*Primary Examiner* — Michael Hobbs
(74) *Attorney, Agent, or Firm* — Roger C. Phillips

(57) ABSTRACT

A hand-held implement for removing microbiological matter from a surface to which the matter is adhered, and storing the matter for subsequent examination, includes a sonic wave generator for producing sonic waves for breaking up a film of the microbiological matter on the surface, a swab for contact with the surface and collecting the microbiological matter, a suction producing device for drawing the microbiological matter from the swab and into the implement, and a trap in the implement for receiving and retaining the drawn biological matter for subsequent examination thereof.

8 Claims, 2 Drawing Sheets

HANDHELD IMPLEMENT FOR REMOVING MICROBIOLOGICAL MATTER FROM A SURFACE

STATEMENT OF GOVERNMENT INTEREST

The invention described herein may be manufactured and used by the United States Government for governmental purposes without the payment of any royalty thereon.

BACKGROUND OF THE INVENTION

1. Field of the Invention

The invention relates to implements for removing microbiological matter from surfaces to which the matter is adhered, and particularly to an implement which dislodges the matter from the surface, draws the dislodged matter into the implement, and stores the drawn-in matter for subsequent examination.

2. Description of the Prior Art

Devices for the collection of microbiological matter from surfaces, such as surfaces in food preparation areas, and on food itself, and on surfaces in medical areas, and the like, are known. Typically, swabs are used to scrub off the microbiological matter and are thereafter examined for harmful bacteria. In many instances, tough films of matter accumulate and harden on a surface, such that soft swabs, such as cotton, sponge, and other resilient materials, are of limited effectiveness in removing the matter from the surface.

Swabs may be soaked in a liquid adapted to aid in the removal of encrusted biological matter and/or may be rough textured to mechanically scrape away such material. Such measures have met with only limited success.

It has been found that sonic waves are effective in breaking up layers of microbiological matter which may then be swabbed up using an ordinary swab. While this represents an improvement in many instances over chemical and/or abrasive mediums, it is not convenient to utilize sonics and mechanical swabs requiring a two step operation followed by still having to test the accumulated matter on the swab, or alternatively, adding still another step of removing the matter from the swab and placing the matter in a test dish or other vehicle.

There is thus a need for an implement which is adapted to loosen microbiological matter adhered to a surface, swab up the loosened matter, and remove the swabbed-up matter from the swab and direct the matter to a collection point at which the matter is stored for handling and subsequent examination.

SUMMARY OF THE INVENTION

An object of the invention is, therefore, to provide an implement having facility for loosening microbiological matter adhered to a surface, for swabbing up the loosened matter, and for transporting the matter from the swab to a collection point thereon at which the swabbed matter can be held for subsequent examination.

With the above and other objects in view, a feature of the present invention is the provision of a hand-held implement for removing microbiological matter from a surface to which the matter is adhered, and storing the matter for subsequent examination, the implement including a sonic wave generator for producing sonic waves for breaking up a film of the microbiological matter on the surface, a swab for contact with the surface and collecting the microbiological matter, a suction producing means for drawing the microbiological matter from the swab and into the implement, and a trap for receiving and retaining the drawn biological matter for subsequent examination thereof.

In accordance with a further feature of the invention, there is provided a sonic swab implement including a housing configured and sized for hand-held operation, a sonic wave generator mounted on the implement and adapted to produce sonic waves for breaking up microbiological material adhered to a surface, a swab mounted on the implement and adapted for engagement with the surface for removal of microbiological material from the surface, a suction producing means mounted on the implement and adapted to draw the microbiological material from the swab, and a trap mounted on the implement and adapted to receive the microbiological material for storage and subsequent examination thereof.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

DESCRIPTION OF THE PREFERRED EMBODIMENTS

Figure 1:
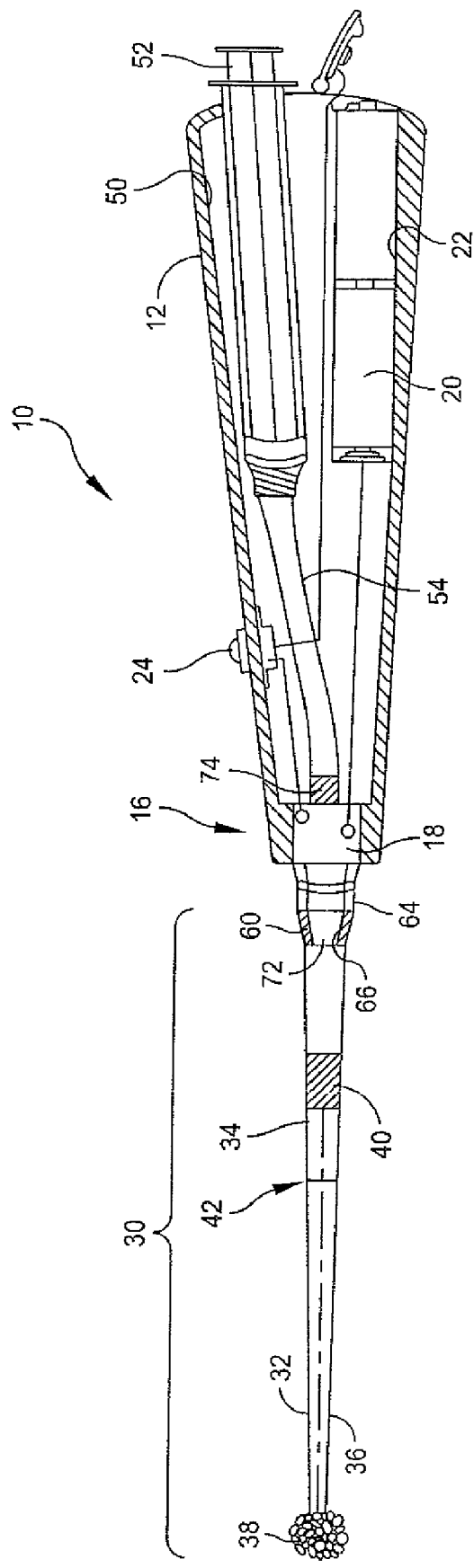
FIG. 1 is a diagrammatic view of an illustrative hand-held implement for removing biological matter from a surface and retaining the removed matter for subsequent examination.

Referring to FIG. 1, it will be seen that an illustrative implement 10 includes a handle 12 adapted to be hand-held by an operator. The handle 12 may be generally conically shaped, as illustrated in FIG. 1, and may be provided with textured surface areas (not shown) to assist in gripping the handle. The handle 12 may, alternatively, be provided with a "pistol" grip, not shown but well known in conjunction with hand-held devices.

On a distal end 16 of the handle 12 there is mounted a sonic horn 18 adapted to emit sound-wave energy for breaking up encrusted or caked layers of microbiological matter disposed on surfaces.

A battery 20 is disposed in a battery compartment 22 in the handle 12. A sonic horn switch 24 is mounted on the handle 12 and is in electrical communication with the battery 20 and the sonic horn 18 for selectively energizing the sonic horn 18.

Figure 2:
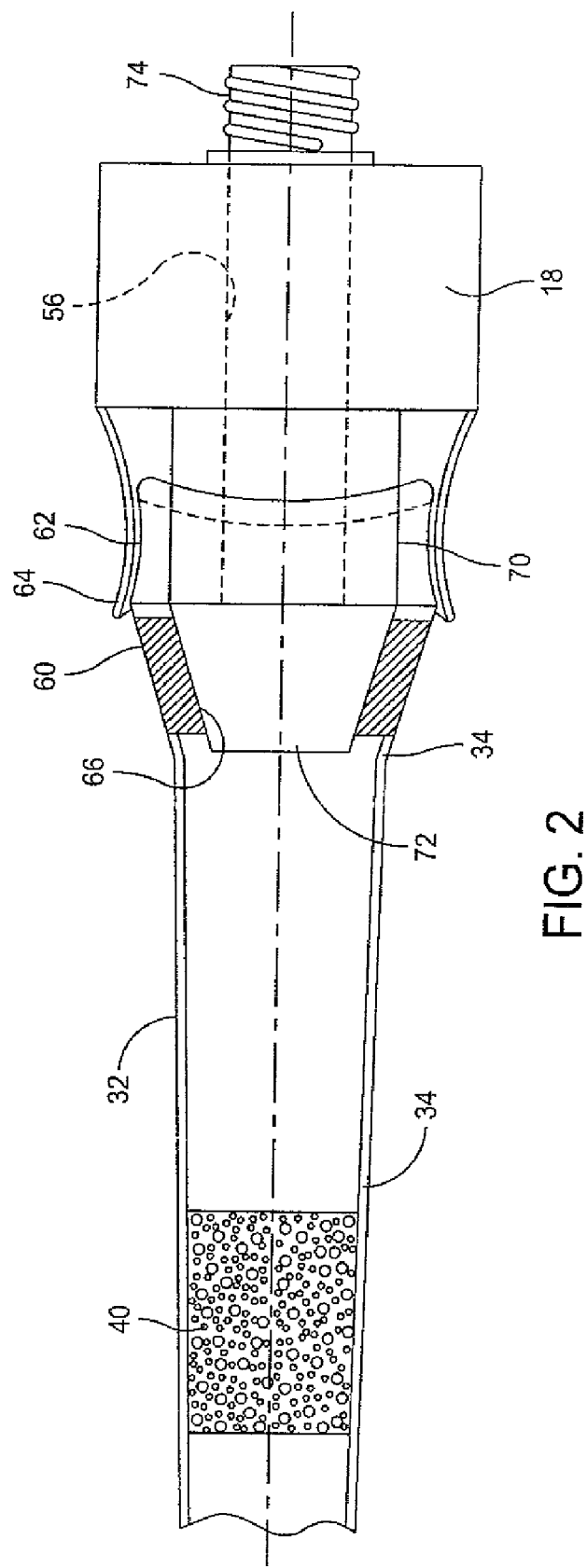
FIG. 2 is an enlarged generally sectional view of a portion of the implement of FIG. 1.

A disposable swab assembly 30 is adapted to be removably mounted on the sonic horn 18. The swab assembly 30 includes an elongated hollow wand 32 having a proximal portion 34 for connection to the sonic horn 18, as shown in FIGS. 1 and 2, and a distal portion 36 having mounted thereon a swab 38.

Disposed within the proximal portion 34 of the wand 32 is a capture filter 40 which extends in circumferential abutment with the internal walls of the proximal portion 34 of the wand 32.

The wand 32 is provided with a weakened juncture 42 between the wand proximal portion 34 and distal portion 36. The weakened juncture 42 is essentially a break point, that is, a point at which the portions 34, 36 of the wand 32 may be easily separated from each other by manual operation.

The swab 38 may be any type commonly used, varying from soft, absorbing, material to a rough-textured material, or a brush. In use, the swab is saturated at least in part with a suitable liquid, such as is currently used in such operations.

The handle 12 includes a further compartment 50 for housing a syringe 52. A tube 54 extends from the syringe 52 to the core of the sonic horn 18 which is provided with a passageway 56 (FIG. 2) extending therethrough and interconnecting the tube 54 and the wand 32.

Referring to FIG. 2, it will be seen that in an exemplary embodiment the swab assembly 34 includes a flaired annular portion 60 of the hollow wand proximal portion 34 and a cylindrically-shaped portion 62. The sonic horn 18 is provided with a flexible distal end portion 64 configured to snugly receive and removably retain the wand proximal end portion 62. The wand proximal annular flaired portion 60 is provided with internal inwardly-directed threads 66 which are engageable with the internal wall of the flaired annular portion of the wand proximal end 60.

The sonic horn 18 is provided proximate the distal end thereof with a cylindrically-shaped barrel portion 70 and, distally thereof, a frusto-conically shaped portion 72.

In affixing the swab assembly 30 to the handle 12, the proximal end portion 34 is pushed onto the barrel portion 70 and frusto-conical portion 72 of the sonic horn 18, as shown in FIG. 2. The cylindrically-shaped portion 62 of the swab assembly proximal end portion 60 slides onto the sonic horn barrel portion 70 and the threads 66 engage the frusto-conically shaped portion of the sonic horn conical portion 72.

The tube 54 extends from the syringe 52 to the sonic horn 18 and is attached thereto by being fitted over a threaded protrusion 74 extending from the sonic horn 18 and in alignment with the sonic horn core passageway 56.

In use, a selected swab 38 is mounted on the distal end of the distal end portion 36 of the wand 32. The swab is soaked with an appropriate liquid. The wand 32 is mounted on the handle 12.

In the collection of microbiological matter, an operator grasps the implement 10 by the handle 12 and manipulates the implement such that the swab, soaked in a liquid, is drawn over the surface from which the microbiological matter is to be taken.

The switch 24 is turned on by the operator and the combination of sonics directed from the sonic horn 18, through the swab assembly hollow wand 32 and through the swab 38, and engagement by the wetted swab causes microbiological matter to be dislodged from the surface being tested and taken into the swab 38.

The operator then manipulates the syringe 52 to draw the liquid, along with the newly acquired matter therein and/or thereon, through the wand 32. The microbiological matter in the drawn liquid is, to a large extent, captured by the capture filter 40, while the drawn liquid continues on through the tube 54 and into the syringe 52.

The swab assembly 30 is then plucked from the sonic horn 18, or handle distal end 16. Pressure applied to the juncture 42 snaps the wand 32 into two portions, permitting easy handling of the proximal portion 34 of the wand 32 and removal of the capture filter 40 therefrom.

The capture filter 40, or the proximal portion 34 of the wand 32 with the capture filter therein, can be moved to an examination and/or analysis location.

Optionally, the syringe 52 may be provided initially with the liquid desired for use with the swab 38. Operation of the syringe forces the liquid through the tube 54 and into the wand 32 and thence into the swab 38. Thus, the syringe may be used to wet the swab, as well as to draw in and hold microbiological matter-bearing liquid.

There is thus provided a hand-held implement which serves to capture microbiological matter off of a surface and retain the matter for subsequent examination.

It will be understood that changes in the details, steps, and arrangement of parts, which have been herein described and illustrated in order to establish the nature of the invention, may be made by those skilled in the art within the principles and scope of the invention as expressed in the appended claims.

What is claimed is:

1. A hand-held implement for removing microbiological matter from a surface to which the matter is adhered, and storing the matter for subsequent examination, the implement comprising:
   a housing comprising a handle and terminating in a handle distal end having an opening;
   a sonic horn located within the housing and being in communication with the opening, the sonic horn being configured to produce sonic waves for passing through the opening and breaking up a film of microbiological matter on a surface;
   a suction producing device also located within the housing and being in fluid communication with the opening, the suction producing device drawing the microbiological matter broken up by the sonic horn into the implement;
   a swab assembly, comprising:
      a wand comprising a generally tubular configuration and having a bore and the wand being configured to be releasably mounted to the handle distal end so that the bore is in fluid communication with the opening, the wand also comprising a break point so that the wand may be broken by hand into two separate portions;
      a swab for contact with the surface and collecting the microbiological matter and the swab being located at an end of the wand distal to the handle and wherethrough sonic waves from the sonic horn pass and the suction of the suction producing device occurs; and
      a trap located within the bore and configured for collecting the drawn biological matter for subsequent examination thereof by functioning of the suction producing device.

2. The implement in accordance with claim 1 wherein said swab comprises a selected one of a body of absorbing material, a brush, and a rough-textured scrubbing medium.

3. The implement in accordance with claim 1 wherein said wand comprises a distal portion located on one side of the break point and adapted to support said swab and a proximal portion located on another side of the break point and wherein said trap is disposed in said proximal portion for ease in removal and testing of the drawn biological material collected in the trap.

4. The implement in accordance with claim 1 wherein said suction producing device comprises a syringe.

5. The implement in accordance with claim 3, further comprising an elastomeric member disposed around a tubular shaped portion of said sonic horn about which the proximal end of said wand may be removably retained.

6. The implement in accordance with claim 5 wherein said tubular shaped portion of said sonic horn and said proximal end of said wand each comprise threads for removably fastening the proximal end of said wand.

7. The implement in accordance with claim 6 wherein the distal end portion of said sonic horn is frusto-conically configured.

8. The implement in accordance with claim 1 wherein said suction producing device comprises a syringe disposed in a compartment in said handle, the compartment and said syringe are provided with releasable interconnection means, such that the syringe is removable from said handle, and the compartment is adapted to connectingly receive a further syringe.

* * * * *